United States Patent [19]

Nagase et al.

[11] Patent Number: 5,395,812
[45] Date of Patent: Mar. 7, 1995

[54] SILVER CATALYST FOR PRODUCTION OF ETHYLENE OXIDE AND METHOD FOR PRODUCTION OF THE CATALYST

[75] Inventors: Shinichi Nagase, Tokyo; Hirohiko Tanabe, Yokohama; Hideki Imai, Hyogo, all of Japan

[73] Assignee: Nippon Shokubai Co., Ltd., Osaka, Japan

[21] Appl. No.: 25,157

[22] Filed: Feb. 25, 1993

[30] Foreign Application Priority Data

Feb. 27, 1992 [JP]  Japan ................................. 4-041303
Dec. 10, 1992 [JP]  Japan ................................. 4-330547

[51] Int. Cl.$^6$ .................... B09J 21/04; B09J 21/08; B09J 21/12; B09J 23/50
[52] U.S. Cl. ................................. 502/238; 502/243; 502/344; 502/347; 502/348; 549/534
[58] Field of Search ............... 502/243, 348, 238, 344, 502/347; 549/534

[56] References Cited

U.S. PATENT DOCUMENTS

| | | |
|---|---|---|
| 3,725,307 | 4/1973 | Brown et al. . |
| 3,925,253 | 12/1975 | Stephens ............................... 502/241 |
| 4,168,247 | 9/1979 | Hayden et al. . |
| 4,368,144 | 1/1983 | Mitsuhata et al. . |
| 4,415,476 | 11/1983 | Ayame et al. . |
| 4,728,634 | 3/1988 | Boxhoorn et al. . |
| 4,769,358 | 9/1988 | Kishimoto et al. ................ 502/348 |
| 5,077,256 | 12/1991 | Yamamoto et al. ................ 502/243 |

FOREIGN PATENT DOCUMENTS 0247414  5/1987  European Pat. Off. .
0380295  1/1990  European Pat. Off. .

*Primary Examiner*—Anthony McFarlane
*Attorney, Agent, or Firm*—Omri M. Behr; Matthew J. McDonald

[57] ABSTRACT

A catalyst for the production of ethylene oxide is disclosed which comprises an α-alumina carrier having the outer surface thereof and the surface of pores therein coated with an amorphous silica-alumina mixture having a total Si and Al content in the range of from $3 \times 10^{-4}$ to $2 \times 10^{-1}$ g/g of carrier and an Si/Al ratio in the range of from 0.05 to 50.0 g/g, 5 to 25% by weight based on perfected catalyst of minute metallic silver particles, and 0.0001 to 0.05 gram equivalent weight per kg of perfected catalyst of cesium. The catalyst, when used for the production of ethylene oxide by the catalytic vapor-phase oxidation of ethylene with molecular oxygen, possesses high selectivity, high activity, and high durability to ensure a long service life.

19 Claims, No Drawings

SILVER CATALYST FOR PRODUCTION OF ETHYLENE OXIDE AND METHOD FOR PRODUCTION OF THE CATALYST

BACKGROUND OF THE INVENTION

1. Field of the Invention

This invention relates to a silver catalyst to be used in the production of ethylene oxide by catalytic vapor-phase oxidation of ethylene with molecular oxygen and to a method for the production of the catalyst.

2. Description of the Prior Art

The catalyst used in the production on a commercial scale of ethylene oxide by catalytic vapor-phase oxidation of ethylene with molecular oxygen is required to possess high selectivity, high activity, and a long service life as essential qualities thereof.

Various studies have been made to date on the preparation of the catalyst with a view to improving the qualities thereof as required. Enormous efforts have been made in the improvement of the carrier, the reaction promotor, and the silver compound. A number of reports which deal with carriers have been published. These include the published specifications of U.S. Pat. No. 3,207,700; Japanese Patent Publication Nos. 43-13,137(1968), 45-21,373(1970), 45-22,419(1970), and 45-11,217(1970); Japanese Pat. Laid-Open No. 57-171,435; U.S. Pat. Nos. 2,766,261, 3,172,893, and 3,664,970. Most of the inventions disclosed therein pertain to micropore distribution and specific surface area of the carrier.

U.S. Pat. No. 2,125,333 discloses an alkali metal salt containing sodium or potassium and a metal salt thereof used as an additive to the silver catalyst for use in the production of ethylene oxide.

U.S. Pat. No. 2,238,474 discloses that sodium hydroxide improves the activity of a catalyst for the production of ethylene, whereas potassium hydroxide exerts an adverse effect on the catalytic action.

U.S. Pat. No. 2,765,283 discloses that a silver catalyst is improved by the addition of an inorganic chloride such as sodium chloride in an amount in the range of from 1 to 2,000 ppm to a catalyst carrier before silver is deposited on the carrier.

U.S. Pat. No. 2,799,687 discloses that a halide such as sodium chloride or potassium chloride present in an amount in the range of from 20 to 16,000 ppm acts as an inhibitor and causes a degradation in the activity of a catalyst.

U.S. Pat. No. 4,007,135 discloses a catalyst for the production of alkylene oxide which contains in the carrier thereof copper, gold, zinc, cadmium, mercury, niobium, tantalum, molybdenum, tungsten, and vanadium, desirably chromium, calcium, magnesium, strontium and/or more preferably vanadium, and equally preferably an alkali metal in an amount exceeding the amount in which they exist naturally in the carrier in the form of impurities or cement and which possess the ability to promote catalysis.

U.S. Pat. No. 4,168,247 discloses a catalyst for the production of alkylene oxide which has silver contained in a porous refractory carrier with a specific surface area in the range of from 0.05 to 10 $m^2/g$ and which further contains in the carrier at least one alkali metal selected from the group consisting of sodium, potassium, rubidium, and cesium in an amount exceeding the amount in which they exist naturally in the carrier in the form of impurities or a binding agent and which promotes catalysis.

U.S. Pat. No. 4,278,562 discloses a catalyst for the production of alkylene oxide produced by first applying silver and optionally sodium or lithium in the form of corresponding salts to a carrier, heating the carrier and deposited salt in the manner generally practised, and thereafter applying thereto alkali metals such as potassium, rubidium, and cerium in the form of salts thereto in combination with an amine and/or ammonia.

Japanese Pat. Laid-Open No. 55-145,677(1980) discloses a silver catalyst for the reaction of oxidation which contains alumina, silica, and titania in a combined amount of not less than 99% by weight and metals of Groups Va, VIa, VIIa, VIII, Ib, and IIb in the Periodic Table of the Elements in the form of metal oxides in a total amount of less than 0.1% by weight and which has silver and optionally an alkali metal component or alkaline earth metal component deposited on a non-oxidizing carrier incapable of assuming an oxidizing color on exposure to methyl red of pKa of +4.8.

U.S. Pat. No. 4,368,144 discloses a silver catalyst for the production of ethylene oxide which comprises an alpha-alumina carrier having a sodium content of not more than 0.07% by weight and a specific surface area in the range of from 0.5 to 5 $m^2/g$, 5 to 25% by weight based on perfected catalyst of metallic silver particles deposited on the carrier, and 0.001 to 0.05 gram equivalent per kg of perfected catalyst of at least one alkali metal or alkali metal compound contained in the carrier in addition to the amount in which the alkali metal or alkali metal compound naturally exists in the carrier.

Japanese Pat. Laid-Open No. 56-105,750(1981) discloses a silver catalyst for the production of ethylene oxide which is obtained by preparing a carrier consisting mainly of alpha-alumina, having a sodium content of not more than 0.07% by weight, and possessing a specific surface area in the range of from 1 to 5 $m^2/g$, subjecting the carrier to an immersing treatment in an immersing liquid having 0.001 to 0.05 gram equivalent per kg of perfected catalyst of a complex of an alkali metal with boron, a complex of an alkali metal with molybdenum, and/or a complex of an alkali metal with tungsten incorporated in a decomposing silver solution such that the ratio of deposition of silver falls in the range of from 5 to 25% by weight based on the amount of the perfected catalyst, and subjecting the impregnated carrier to thermal reduction or thermal decomposition.

Japanese Pat. Laid-Open No. 57-107,241(1982) discloses a silver catalyst for the production of ethylene oxide which contains at least sodium (Na) as a cationic component and chlorine (Cl) as an anionic component besides silver in amounts such that the atomic ratio of Cl/Na is less than 1.

U.S. Pat. No. 4,415,476 discloses a silver catalyst for the production of ethylene oxide which contains at least sodium and cesium as cationic components and chlorine as chloride as an anionic component in addition to the silver.

E.P. 247414 discloses a silver catalyst for the production of ethylene oxide which contains at least sodium, potassium, rubidium, and/or cesium as cationic components in addition to silver as a catalytic component and uses a carrier consisting mainly of alpha-alumina and having a surface area in the range of from 0.6 to 2 $m^2/g$, an absorption ratio in the range of from 20 to 50%, a silica content in the range of from 0.5 to 12% by weight, a silica content in the range of from 0.5 to 12, preferably from 1 to 8, (weight %/m$^2$/g) per surface area, and a sodium content in the range of from 0.08 to 2% by weight.

Numerous pertinent reports have been published as demonstrated above and most of them are directed to enhancing the catalytic qualities of a silver catalyst by the addition of alkali metals falling in a limited range to the silver catalyst. Though the catalysts disclosed therein exhibit ideal initial catalytic properties, they are deficient in terms of service life.

The carriers used in the silver catalysts for the production of ethylene oxide have many problems not yet elucidated and required to be further improved. For example, the choice of composition of the components for the carrier, the physical properties of carrier such as specific surface area, pore diameter, pore size distribution, pore volume, porosity, particle diameter, and particle shape, and the chemical properties of such carrier materials as alpha-alumina, silicon carbide, silica, and zirconia remain yet to be improved for optimization.

An object of this invention, therefore, is to provide a novel silver catalyst for the production of ethylene oxide which combines high selectivity, high activity, and a lasting service life.

Another object of this invention is to provide a novel silver catalyst for the production of ethylene oxide which enjoys an enhanced service life owing to the use of an alpha-alumina carrier having a specific surface area in the range of from 0.75 to 5 m$^2$/g and an apparent porosity in the range of from 45 to 70%.

The present inventors have been pursuing a study concerning the composition of components and the specific surface area of an ideal carrier to be used in a silver catalyst for the production-of ethylene oxide. As disclosed in U.S. Pat. No. 5,077,256, they have already developed a silver catalyst which is able to exhibit high selectivity and maintain this high selectivity for a long time by using an alpha-alumina carrier having the outer surface thereof and the surface of the pores therein coated with amorphous silica. After further continuing the study, they have found that a silver catalyst using an alpha-alumina carrier having the outer surface of carrier and the surface of pores therein coated with an amorphous silica-alumina mixture exhibits higher selectivity and maintains this higher selectivity for a longer time than the silver catalyst using the amorphous silica coating on the outer surface of carrier and the surface of pores therein. This invention has been perfected as a result.

SUMMARY OF THE INVENTION

The objects described above are accomplished by a silver catalyst for the production of ethylene oxide which comprises an α-alumina carrier having the outer surface of carrier and the surface of pores therein coated with an amorphous silica-alumina mixture and having a total Si and Al content in the amorphous silica-alumina mixture in the range from $33 \times 10^{-4}$ to $2 \times 10^{-1}$ g/g of carrier and a Si/Al ratio in the amorphous mixture in the range of from 0.05 to 50.0 g/g and 5 to 25% by weight based on perfected catalyst of minute metallic silver particles and 0.0001 to 0.05 gram equivalent per kg of perfected catalyst of cesium deposited on the α-alumina carrier.

The objects described above are also accomplished by a method for the production of a silver catalyst for the manufacture of ethylene oxide, which comprises adopting as a main material an alumina powder having a secondary particle diameter in the range of from 20 to 200 μm formed of primary α-alumina particles 0.1 to 10 μm in diameter and a specific surface area in the range of from 0.1 to 10 m$^2$/g mixing the alumina powder with alumina and silica which are in a colloidal state, molding the resultant mixture in a prescribed shape, drying the molded article and calcining it at a temperature in the range of from 1,000° to 1,600° C. thereby preparing an alpha-alumina carrier having the outer surface thereof and the surface of pores therein coated with an amorphous silica-alumina mixture having a total Si and Al content in the range of from $3 \times 10^{-4}$ to $2 \times 10^{-1}$ g/g of carrier and an Si/Al ratio in the amorphous mixture in the range of from 0.05 to 50.0 g/g, depositing 5 to 25% by weight based on perfected catalyst of minute metallic silver particles and 0.0001 to 0.05 gram equivalent weight per kg of perfected catalyst of cesium on the α-alumina carrier, then subjecting the catalyst component-deposited carrier to an activating treatment thereby giving rise to deposition of silver and cesium on a porous inorganic refractory carrier, and thereafter subjecting the produced precursory catalyst to a heat treatment in an inert gas at a temperature in the range of from 400° to 950° C.

The present invention produces a novel silver catalyst for the production of ethylene oxide which is able to exhibit high selectivity and maintain the high activity for a long time by using an α-alumina carrier having the outer surface of carrier and the surface of pores therein coated with an amorphous silica-alumina mixture whose Si and Al contents account for a prescribed ratio and depositing on the α-alumina carrier 5 to 25% by weight based on perfected catalyst of minute metallic silver particles and 0.0001 to 0.05 gram equivalent weight per kg of perfected catalyst of cesium.

DESCRIPTION OF THE PREFERRED EMBODIMENT

An α-alumina carrier exhibiting a specific surface area in the range of from 0.75 to 5 m$^2$/g and an apparent porosity in the range of from 45 to 70% and having the outer surface of carrier and the surface of pores therein coated with an amorphous silica, according to the research on ideal carriers for use in silver catalysts for the production of ethylene oxide, has not found popular acceptance in the commercial-scale applications on account of lower selectivity in catalysis as compared with the carrier heretofore adopted generally for the commercial-scale applications of catalysis. Even this carrier of relatively high specific surface area can be effectively utilized in the present invention. It has been found in the present invention that the catalyst which is obtained by depositing on this carrier cesium and/or a cesium compound as a reaction promoter, then subjecting the reaction promoter-deposited carrier to an activation treatment thereby inducing deposition of silver and cesium and/or cesium compound on the α-alumina carrier, and heat-treating the resultant precursory catalyst in an inert gas at an elevated temperatures in the range of from 400° to 950° C. exhibits activity, selectivity, and durability at heretofore unattainable high levels.

The catalysts to be used in the production of ethylene oxide by the catalytic vapor-phase oxidation of ethylene with molecular oxygen are silver catalysts. It goes without saying that most of these silver catalysts are supported catalysts using a carrier. It is also universally known that the carriers to be used in supported catalysts are porous granular refractory materials.

The porous granular refractory carriers, though simple in utterance, are widely varied. The physical properties such as specific surface area, pore size distribution, pore volume, particle diameter, and shape which are possessed by such carriers and the chemical properties possessed by α-alumina, silica, silicon carbide, zirconia, and clay which are components for carriers have profound effects on the qualities of catalysts produced with these carriers.

The quality of the carrier to be selected is a grave problem for most persons of ordinary skill in the art. Of the properties of the carrier, the specific surface area dictates close attention because it bears on the pore diameter and exerts a great influence on the catalyst behavior. Specifically, from the standpoint of activity and durability, the specific surface area of catalyst is preferably large and the specific surface area of the carrier is consequently preferably large. For the carrier to have a large specific surface area, the alumina particles selected as the material for carrier must be of a small diameter. This requirement necessarily implies formation of pores of a small diameter. This fact proves to be disadvantageous in respect of diffusion and stagnation of gas and removal of the heat of reaction. It is further disadvantageous in that the surface of exposure of the carrier is prone to increase. These factors invariably result in a decline of the selectivity In the light of these facts, it is not always right to say that the specific surface area should be larger than not. This property has its own limit. Most of the carriers heretofore adopted on a commercial scale have specific surface areas of not more than 1 $m^2/g$, even not more than 0.5 $m^2/g$. Exceptionally, some of these carriers have specific surface areas exceeding 1 $m^2/g$ and they are more deficient in selectivity than those of smaller specific surface areas.

We have continued a study in search of a way of eliminating the drawbacks mentioned above and have consequently found a method for maintaining and promoting high activity and durability of a carrier with a specific surface area of not less than 0.75 $m^2/g$ while improving and not sacrificing selectivity. A silver catalyst using an α-alumina alumina carrier of the present invention which has the outer surface of carrier and the surface of pores therein coated with an amorphous silica-alumina mixture, when adopted for the production of ethylene oxide, exhibits higher selectivity and retains this selectivity for a longer time than that using the α-alumina carrier having the outer surface of carrier and the surface of pores therein as already disclosed by us in U.S. Pat. No. 5,077,256. This fact is conspicuous in a carrier having a high specific surface area of not less than 0.75 $m^2/g$ and in a catalyst incorporating therein an increased amount of a cesium compound. It is surprising to note that the aforementioned disadvantage from the standpoint of physical properties is overcome more effectively by improving the chemical properties of carrier, namely by using the α-alumina carrier having the outer surface of carrier and the surface of pores therein with the amorphous silica-alumina mixture instead of the α-alumina carrier using an amorphous silica coat. The specific surface areas mentioned in the specification hereof are numerical values determined by the Bruneuer-Emmett-Teller (hereinafter referred to briefly as "BET") method.

In accordance with the present invention, the outer surface of carrier and the surface of pores therein delicately affect the catalytic performance. The adverse phase of the effect decreases in proportion as the specific surface area decreases and gradually increases as the specific surface area exceeds 0.5 $m^2/g$ and becomes conspicuous as the surface area exceeds 0.75 $m^2/g$.

Owing to the α-alumina carrier of our former development having the outer surface of carrier and the surface of pores therein coated with an amorphous silica has permitted use of a carrier having a theretofore impracticable specific surface area exceeding 0.75 $m^2/g$. It has been established by the present invention that a silver catalyst which uses the α-alumina carrier of the present invention having the outer surface of carrier and the surface of pures therein coated with an amorphous silica-alumina mixture, when used in producing ethylene oxide, exhibits better activity and selectivity than that using the α-alumina carrier having the outer surface of carrier and the surface of pores therein with an amorphous silica.

Though the improvement enjoyed by the catalyst depends more or less on the properties of the carrier as demonstrated in the working examples to be cited herein below, the incorporation of cesium in the catalyst makes the distinction in service life stand out to a surprising extent. The mechanism which is responsible for the excellent service life remains yet to be elucidated. The substance to coat the outer surface of carrier and the surface of pores therein performs better when it is an amorphous silica-alumina mixture than when it is an amorphous silica. The catalyst which is obtained by depositing cesium on the carrier, then subjecting the cesium-deposited carrier to an activating treatment thereby inducing deposition of silver and cesium and/or a cesium compound on a porous inorganic refractory carrier, and heat-treating the resultant precursory catalyst in an inert gas at an elevated temperature in the range of from 400° to 950° C. enjoys an improvement of about 1% in selectivity as compared with the catalyst using an amorphous silica. It is reported in the literature that the adsorption of metallic ions onto alumina and silica depends greatly on pH. In consideration of these facts, it is logically concluded that the amorphous silica-alumina mixture, rather than the amorphous silica deposited on the outer surface of the carrier and the surface of pores therein, when impregnated with a solution containing silver and cesium, affects more strongly the distribution of deposition of silver and, to a greater extent, of cesium and the binding force of such deposited metals with the carrier. This fact seems to bear on the catalytic performance.

Ideally, the amount of cesium and/or cesium compound to be added in this invention is in the range of from 0.0001 to 0.05 gram equivalent weight, preferably from 0.001 to 0.03 gram equivalent weight, per kg of perfected catalyst. Particularly, this amount is desired to exceed 0,008 gram equivalent weight and to be not more than 0.03 gram equivalent weight.

The specific surface area of the α-alumina carrier to be used effectively in this invention is in the range of from 0.75 to 5 $m^2/g$, preferably from 0.8 to 2 $m^2/g$. If the specific surface area exceeds 5 $m^2/g$, the carrier fails to acquire subsantially satisfactory quality. The carrier components other than α-alumina and sodium (mainly $Na_2O$) are desired to be those which are commonly contained in carriers passing in the field and in such amounts as accepted commonly in the field.

The apparent porosity of the α-alumina carrier of this invention is desired to be in the range of from 45 to 70%, preferably from 50 to 60%.

The specific pore volume of the α-alumina carrier of this invention is desired to be in the range of 0.1 to 0.8 cc/g, preferably 0.2 to 0.5 cc/g.

The α-alumina carrier which is effectively used in the present invention is an α-alumina carrier comprising mainly an α-alumina having a particle diameter in the range of from 3 to 20 mm, preferably an alumina powder having an α-alumina content of not less than 90% by weight, possessing a secondary particle diameter in the range of from 20 to 200 μm formed of primary α-alumina particles 0.1 to 10 μm in diameter and possessing a specific surface area in the range of from 0.1 to 10 m²/g. The carrier to be used in the present invention is a refractory carrier in the form of spheres, pellets, rings, and other particulate pieces. The average equivalent diameter is in the range of from 3 to 20 mm, preferably from 5 to 10 mm. Particularly, the composition of components for the carrier and the specific surface area of the carrier bear largely on the catalyst performance. In the manufacture of the catalyst, the selection of a carrier shape capable of facilitating uniform deposition of silver and cesium and/or cesium compound on the carrier forms the key to successful production of a catalyst excelling in selectivity.

The α-alumina carrier is preferable, for example, to be formed mainly of an α-alumina having a BET specific surface area in the range of from 0.8 to 2 m²/g, an apparent porosity in the range of from 50 to 60%, a pore volume in the range of from 0.2 to 0.5 cc/g, and a particle diameter in the range of from 3 to 20 mm, preferably a carrier of an α-alumina content of not less than 90% by weight. Ideally, this α-alumina carrier has the outer surface thereof and the surface of pores therein coated with an amorphous silica-alumina mixture and is obtained by adopting as a main raw material, an alumina powder having a secondary particle diameter in the range of from 20 to 200 μm formed of primary α-alumina particles 0.1 to 10 μm in diameter and possessing a specific surface area in the range of from 0.1 to 10 m²/g, preferably from 1 to 5 m²/g, mixing this main raw material with alumina and silica particles having a diameter in the range of from 1 to 300 nm, preferably from 1 to 20 nm, and assuming a colloidal form, thoroughly kneading the resultant mixture with an organic binding agent and water commonly used in the pelletization of carrier by the use of a blending device such as a kneader, extrusion molding and pelletizing the blend, drying the resultant pellets, and firing them at a temperature in the range of from 1,000° to 1,600° C., preferably from 1,200° to 1,500° C., for a period in the range of from 1 to 10 hours, preferably from 2 to 10 hours.

The alumina and silica particles having a diameter in the range of from 1 to 300 nm are generally preferable to be used in the form of an aqueous solution of alumina sol and colloidal silica on account of ease of dispersion. The preparation of alumina sol and colloidal silica is dealt with in "Handbook on Development and Application of Ultrafine Powder," Apr. 5, 1989, Science Forum K.K.

The alumina sol can be produced by a method which comprises hydrolyzing an aluminum salt or a method which comprises neutralizing an aqueous aluminum salt solution with an alkali thereby forming a gel provisionally and subsequently deflocoulating the gel.

The colloidal silica can be produced by a method which comprises neutralizing an aqueous sodium silicate solution with an acid thereby forming a gel provisionally and subsequently deflocculating the gel or a method which comprises subjecting an aqueous sodium silicate solution to ion exchange thereby expelling sodium from the solution. As commercial products of alumina sol, "Alumina Sol 100, Alumina Sol 200, and Alumina Sol 500" which are marketed by Nissan Chemical Industry Co. Ltd. are available. As a commercial product of colloidal silica, "Snowtex O" marketed by Nissan Chemical Industry Co., Ltd. is available.

The α-alumina carrier of the present invention ideally contain an amorphous silica-alumina mixture so that the total Si and Al content per gram of carrier falls in the range of from $3 \times 10^{-4}$ to $2 \times 10^{-1}$ g/g of carrier, preferably from $5 \times 10^{-4}$ to $1 \times 10^{-1}$ g/g of carrier. Particularly preferably, the α-alumina carrier has an amorphous silica-alumina mixture content such that the Si/Al ratio is in the range of from 0.05 to 50.0, preferably from 0.5 to 10.0.

For the preparation of the catalyst is adopted a method which comprises impregnating the carrier of the kind described above with an aqueous solution or solvent solution of a decomposable silver salt such as, for example, an aqueous silver nitrate solution, an ammonia complex of the silver salt of an inorganic or organic acid, an amine complex of the silver salt of an organic acid, or an aqueous silver lactate solution. Cesium and/or a cesium compound can be deposited preparatorily on the carrier or it can be incorporated in a silver solution and then deposited simultaneously with silver on the carrier. Otherwise, it can be deposited on the carrier which has undergone a step for decomposition and reduction of silver and a subsequent step for decomposition and expulsion and which consequently has silver deposited thereon. Then, the impregnated carrier produced as a consequence is heated to decompose or reduce the decomposable silver salt and the product of this decomposition is decomposed and removed with a heated gas.

For the preparation of a catalyst using the α-alumina carrier of the present invention, specifically a silver catalyst to be used in the manufacture of ethylene oxide by the catalytic vapor-phase oxidation of ethylene with molecular oxygen, a method can be adopted which comprises adopting an α-alumina carrier of this invention, impregnating this carrier with a solution of a decomposable silver salt such as an amine complex of the silver salt of an organic acid, heating the impregnated carrier to a temperature in the range of from 100° to 300° C. to effect reduction or thermal decomposition and induce deposition of silver and cesium and/or a cesium compound on a porous inorganic refractory carrier, and finally heat-treating the resultant precursory catalyst in an inert gas containing oxygen in a concentration of not more than 3% by volume at an elevated temperature in the range of from 400° to 950° C., preferably from 500° to 800° C. In the silver catalyst of the present invention, the silver can be deposited in the form of minute particles on the inner and outer surfaces of the carrier in an amount in the range of from 5 to 25% by weight, preferably from 5 to 20% by weight, based on the amount of the catalyst. The cesium or cesium compound is added in the form of an aqueous solution or alcoholic solution in an amount in the range of from 0.0001 to 0.05 gram equivalent weight, preferably in the range between the lower limit of 0.003 gram equivalent weight and the upper limit of 0.03 gram equivalent weight, to a silver solution and caused to be deposited simultaneously with the silver. Otherwise, it may be deposited on the carrier either before or after the silver has been deposited thereon.

The reaction conditions to be adopted for the production of ethylene oxide by the oxidation of ethylene with molecular oxygen through the agency of the silver catalyst of the present invention can be selected from all of the conditions heretofore known in the art. Specifically, the general conditions adopted for commercial-scale production, i.e. a raw material gas composition comprising 0.5 to 40% by volume of ethylene, 3 to 10% by volume of oxygen, 5 to 30% by volume of carbon dioxide, and the balance to make up 100% by volume of such inert gas as nitrogen, argon, and steam, a lower hydrocarbon such as methane and ethane, ethylene dichloride as a reaction inhibitor, and a halide such as diphenyl chloride, a space velocity in the range of from 1,000 to 30,000 $hr^{-1}$(STP), preferably from 3,000 to 8,000 $hr^{-1}$ (STP), and a pressure in the range of from 2 to 40 $kg/cm^2 G$, preferably from 15 to 40 $kg/cm^2 G$, can be advantageously used.

Now, the present invention will be described more specifically below with reference to working examples and controls. The present invention may be practised otherwise without departing from the spirit of the present invention. The magnitudes of conversion and selectivity which are mentioned in the working examples and controls are numerical values by the calculations of the following formulas.

Conversion (%)=[(Number of mols of ethylene consumed in reaction/Number of mols of ethylene in raw gas)]×100

Selectivity (%)=[(Number of mols of ethylene converted into ethylene oxide/Number of mols of ethylene consumed in reaction)]×100

Method of production of carrier A

In a kneader, 93 parts by weight of a commercially available alumina powder (having a primary particle diameter of α-alumina of 1 to 2 μm, an average secondary particle diameter of 50 to 60 μm, and a BET specific surface area of 2.5 to 3.5 $m^2/g$) and 5 parts by weight of an organic binding agent were thoroughly mixed. The resultant mixture in the kneader and 4 parts by weight (as $Al_2O_3$ content) of an alumina sol having a particle diameter in the range of from 2 to 20 nm, 3 parts by weight (as $SiO_2$ content) of a colloidal silica having a particle diameter in the range of from 2 to 20 nm, and 40 parts by weight of water added thereto were thoroughly mixed. The resultant alumina mixture was extrusion molded, pelletized, and then dried at 1,450° C. for 2 hours to obtain a carrier. The product was an α-alumina carrier possessing a BET specific surface area of 1.26 $m^2/g$, an apparent porosity of 55.7%, and a pore volume of 0.40 cc/g, having the outer surface thereof and the surface of pores therein coated with an amorphous silica-alumina mixture, and assuming the form of rings measuring 7 mm in outside diameter, 3 mm in inside diameter, and 7 mm in length. It was designated as Carrier A. By the method of determination indicated below, the silica content and the alumina content in the amorphous silica-alumina mixture deposited on the Carrier A were found respectively to be $1.2 \times 10^{-2}$ g/g of carrier and $1.0 \times 10^{-2}$ g/g of carrier, the Si/Al ratio being 1.2 g/g.

Method for determination of silica and alumina contents of amorphous silica-alumina mixture deposited on outer surface of α-alumina carrier A and on surface of pores therein A log sample of the carrier was pulverized to a size of 8 to 10 mesh, immersed in 20 ml of an aqueous 46 wt % hydrogen fluoride solution at normal room temperature for 1 hour, and filtered. The solution obtained as a filtrate was tested for Si ion concentration and Al ion concentration by the use of an atomic absorption analyzer.

EXAMPLE 1

A slurry obtained by blending 830 g of silver oxalate with 200 ml of water was thoroughly stirred with 700 ml of ethanolamine. The resultant solution and 100 ml of water added thereto were thoroughly stirred. The produced mixture and a solution of 7.5 g of cesium nitrate in 200 ml of water were stirred to prepare an impregnating solution.

In this impregnating solution, 3,000 g of the α-alumina carrier heated in advance to about 100° C. was left standing for impregnation, heated for concentration, dried, further heated in an air bath at 120° C. for 3 hours, and then activated in a current of air at 280° C. for 48 hours.

The precursory catalyst thus obtained was placed in a tightly closed stainless steel vessel adapted to introduce an inert gas from an external source. In an electric furnace which was swept with nitrogen gas, the catalyst bed in the vessel was heat-treated at a temperature of 530° C. for 3 hours to produce a finished catalyst.

The perfected catalyst was found to have a total cesium content of $11 \times 10^{-3}$ gram equivalent weight per kg of catalyst.

Method for determination of total cesium content of perfected catalyst

A sample, about 20 g, of the perfected catalyst was powdered and compressed. (at a pressure of 20 $kg/cm^2$) into a test sheet. A sample catalyst of a known cesium concentration was similarly treated and used as a standard. The test sheet was tested with a fluorescent X-ray spectroscope and the result of this test was evaluated in accordance with a calculating graph obtained of the recorded data of the standard sample. As a result, the total cesium content was found to be 0.15% by weight. This value indicates that the total cesium content of the perfected catalyst was $11 \times 10^{-3}$ gram equivalent weight per kg of catalyst.

The perfected catalyst was placed in an externally heated type double-pipe stainless steel reaction vessel 25 mm in inside diameter and 11,000 mm in length. To the catalyst bed thus formed, a mixed gas consisting of 20% by volume of ethylene, 7% by volume of oxygen, 7% by volume of carbon dioxide, and the balance of methane, nitrogen, argon, and ethane and further containing 1 ppm of ethylene dichloride was introduced. The catalyst bed as the site of the reaction was heated at a reaction pressure of 24 $kg/cm^2G$, a space velocity of 5,500 $hr^{-1}$, and a heat medium temperature of 230° C. to induce a reaction. The results of the reaction after 10 days of continued operation and those of the reaction after one year of continued operation are shown in Table 1.

EXAMPLE 2

An oxidation was carried out by following the procedure of Example 1, except that the heat treatment was performed under the conditions shown in Table 1. The results of the reaction after 10 days of continued operation and those of the reaction after one year of continued operation are shown in Table 1.

EXAMPLES 3 and 4

Oxidations were carried out by following the procedure of Example 1, except that carriers shown in Table 1 were used instead. The results of the reaction after 10 days of continued operation and those of the reaction after 1 year of continued operation are shown in Table 1.

Controls 1 and 2

Operations were carried out by following the procedure of Example 1 except that the heat treatment was performed under the conditions shown in Table 2. The results of the reaction after 10 days of continued operation and those of the reaction after one year of continued operation are shown in Table 2.

Control 3

An operation was carried out by following the procedure of Example 1, except that a commercially available carrier (produced by Norton Co. and marketed under product code of "SA-5205") was used in its unaltered form. The results of the reaction after 10 days of continued operation and those of the reaction after one year of continued operation are shown in Table 2.

Control 4

An operation was carried out by following the procedure of Example 1, except that a commercially available carrier (produced by Norton Co. and marketed under product code of "SA-5102") was used in its unaltered form. The results of the reaction after 10 days of continued operation and those of the reaction after one year of continued operation are shown in Table 2.

Controls 5 and 6

An operation was carried out by following the procedure of Example 1, except that a carrier produced by impregnating a carrier (produced by Norton Co. and marketed under product code of "SA-5102") with colloidal silica (2 to 50 nm), heating the impregnated carrier for concentration, drying and calcining at 1,000° C. for 5 hours and coated on the outer surface of the carrier and the surface of the pores therein with an amorphous silica was used instead, and the coated carrier was subjected to a high temperature heat treatment at a temperature shown in Table 2. The results of the reaction after 10 days of continued operation and those of the reaction after one year of continued operation are shown in Table 2.

Control 7

An operation was carried out by following the procedure of Example 1, except that a carrier produced by Norton Co. and marketed under product code of SA-5102 was used in its unaltered form, the cesium content was as shown in Table 2, and the heat treatment was omitted. The results of the reaction after 10 days of continued operation and those of the reaction after one year of continued operation are shown in Table 2.

Control 8

An operation was carried out by following the procedure of Example 1, except that the cesium content was as shown in Table 2 and the heat treatment was omitted. The results of the reaction after 10 days of continued operation and those of the reaction after one year of continued operation are shown in Table 2.

TABLE 1

|  | Example | | | |
| --- | --- | --- | --- | --- |
|  | 1 | 2 | 3 | 4 |
| (Properties of carrier) | | | | |
| Specific surface area (m$^2$/g) | 1.26 | 1.26 | 1.43 | 1.15 |
| Apparent porosity (%) | 55.7 | 55.7 | 58.2 | 57.5 |
| Apparent pore volume (cc/g) | 0.40 | 0.40 | 0.41 | 0.37 |
| (Composition) | | | | |
| α-Al$_2$O$_3$ (wt %) | 93.0 | 93.0 | 98.0 | 80.0 |
| Amount of amorphous silica-alumina on the surface of carrier | | | | |
| (Si g/g carrier) | $1.2 \times 10^{-2}$ | $1.2 \times 10^{-2}$ | $2 \times 10^{-4}$ | $9 \times 10^{-2}$ |
| (Al g/g carrier) | $1.0 \times 10^{-2}$ | $1.0 \times 10^{-2}$ | $3 \times 10^{-4}$ | $1 \times 10^{-2}$ |
| (Si + Al g/g carrier) | $2.2 \times 10^{-2}$ | $2.2 \times 10^{-2}$ | $5 \times 10^{-4}$ | $1 \times 10^{-1}$ |
| Si/Al ratio (g/g) | 1.2 | 1.2 | 0.67 | 9.0 |
| Supporting ratio of silver in perfected catalyst (wt %) | 15 | 15 | 15 | 15 |
| Amount of cesium in perfected catalyst (gram equivalent weight/kg catalyst) | $11 \times 10^{-3}$ | $25 \times 10^{-3}$ | $11 \times 10^{-3}$ | $11 \times 10^{-3}$ |
| High temperature heat treatment temperature (°C.) | 530 | 650 | 530 | 530 |
| High temperature heat treatment time (hr) | 3 | 3 | 3 | 3 |
| Reaction result | | | | |
| (After 10 days) | | | | |
| Reaction temperature (°C.) | 230 | 230 | 230 | 228 |
| Conversion (%) | 10 | 10 | 10 | 10 |
| Selectivity (%) | 82.0 | 81.9 | 81.8 | 81.8 |
| (After 1 year) | | | | |
| Reaction temperature (°C.) | 231 | 231 | 231 | 229 |
| Conversion (%) | 10 | 10 | 10 | 10 |

TABLE 1-continued

| | Example | | | |
|---|---|---|---|---|
| | 1 | 2 | 3 | 4 |
| Selectivity (%) | 81.8 | 81.7 | 81.6 | 81.5 |

TABLE 2

| | Control | | | | | | | |
|---|---|---|---|---|---|---|---|---|
| | 1 | 2 | 3 | 4 | 5 | 6 | 7 | 8 |
| (Properties of carrier) | | | | | | | | |
| Specific surface area (m²/g) | 1.26 | 1.26 | 0.03 | 0.89 | 0.89 | 0.89 | 0.89 | 1.26 |
| Apparent porosity (%) | 55.7 | 55.7 | 52.3 | 52.8 | 52.8 | 52.8 | 52.8 | 55.7 |
| Apparent pore volume (cc/g) | 0.40 | 0.40 | 0.31 | 0.28 | 0.28 | 0.28 | 0.28 | 0.40 |
| (Composition) | | | | | | | | |
| α-Al₂O₃ (wt %) | 93.0 | 93.0 | 86.1 | 98.9 | 98.4 | 98.4 | 98.9 | 93.0 |
| Amount of amorphous silica-alumina on the surface of carrier | | | | | | | | |
| (Si g/g carrier) | $1.2 \times 10^{-2}$ | $1.2 \times 10^{-2}$ | $2 \times 10^{-4}$ | $1.5 \times 10^{-4}$ | $5.0 \times 10^{-3}$ | $5.0 \times 10^{-3}$ | $1.5 \times 10^{-4}$ | $1.2 \times 10^{-2}$ |
| (Al g/g carrier) | $1.0 \times 10^{-2}$ | $1.0 \times 10^{-2}$ | $1 \times 10^{-5}$ | $1.0 \times 10^{-5}$ | $1.0 \times 10^{-5}$ | $1.0 \times 10^{-5}$ | $1.0 \times 10^{-5}$ | $1.0 \times 10^{-2}$ |
| (Si + Al g/g carrier) | $2.2 \times 10^{-2}$ | $2.2 \times 10^{-2}$ | $2.5 \times 10^{-4}$ | $1.6 \times 10^{-4}$ | $5.0 \times 10^{-3}$ | $5.0 \times 10^{-3}$ | $1.6 \times 10^{-4}$ | $2.2 \times 10^{-2}$ |
| Si/Al ratio (g/g) | 1.2 | 1.2 | 2.0 | 15.0 | 500 | 500 | 15.0 | 1.2 |
| Supporting ratio of silver in perfected catalyst (wt %) | 15 | 15 | 15 | 15 | 15 | 15 | 15 | 15 |
| Amount of cesium in perfected catalyst (gram equivalent weight/kg catalyst) | $11 \times 10^{-3}$ | $11 \times 10^{-3}$ | $11 \times 10^{-3}$ | $11 \times 10^{-3}$ | $11 \times 10^{-3}$ | $11 \times 10^{-3}$ | $3 \times 10^{-3}$ | $3 \times 10^{-3}$ |
| High temperature heat treatment temperature (°C.) | — | 300 | 530 | 530 | 600 | 700 | — | — |
| High temperature heat treatment time (hr) | — | 3 | 3 | 3 | 3 | 3 | — | — |
| Reaction result | | | | | | | | |
| (After 10 days) | | | | | | | | |
| Reaction temperature (°C.) | Not reacted | Not reacted | Not reacted | Not reacted | 233 | 233 | 230 | 228 |
| Conversion (%) | | | | | 10 | 10 | 10 | 10 |
| Selectivity (%) | | | | | 81.0 | 81.0 | 78.5 | 79.3 |
| (After 1 year) | | | | | | | | |
| Reaction temperature (°C.) | — | — | — | — | 236 | 236 | 235 | 233 |
| Conversion (%) | | | | | 10 | 10 | 10 | 10 |
| Selectivity (%) | | | | | 80.5 | 80.5 | 76.5 | 77.5 |

What is claimed is:

1. A silver catalyst for the production of ethylene oxide, comprising an α-alumina carrier having the outer surface thereof and the surface of pores therein coated with an amorphous silica-alumina mixture having a total Si and Al content in the range of from $3 \times 10^{-4}$ to $2 \times 10^{-1}$ g/g of carrier and an Si/Al ratio in the range of from 0.05 to 50.0 g/g and 5 to 25% by weight based on finished catalyst of fine metallic silver particles and 0.0001 to 0.05 gram equivalent weight per kg of finished catalyst of cesium, said silver and said cesium being deposited on said α-alumina carrier.

2. A catalyst according to claim 1, wherein the specific surface area of said α-alumina carrier is in the range of from 0.75 to 5 m²/g.

3. A catalyst according to claim 2, wherein the apparent porosity of said α-alumina carrier is in the range of from 45 to 70%.

4. A catalyst according to claim 2, wherein said cesium content is in the range of from 0.001 to 0.03 gram equivalent weight per kg of finished catalyst.

5. A catalyst according to claim 3, wherein the specific pore volume of said α-alumina carrier is in the range of from 0.1 to 0.8 cc/g.

6. A catalyst according to claim 2, wherein the total metallic silver content is in the range of from 5 to 20% by weight based on the amount of finished catalyst.

7. A catalyst according to claim 2, wherein the coating of said amorphous silica-alumina mixture has a total Si and Al content in the range of from $5 \times 10^{-4}$ to $1 \times 10^{-1}$ g/g of carrier and an Si/Al ratio in the range of from 0.5 to 10.0 g/g.

8. A catalyst according to claim 1, wherein said α-alumina carrier has as a main component thereof secondary α-alumina particles 20 to 200 μm in diameter formed of primary α-alumina particles 0.1 to 10 μm in diameter.

9. A catalyst according to claim 1, wherein said carrier has pores of an average equivalent diameter in the range of from 3 to 20 mm.

10. A catalyst according to claim 1, wherein the specific pore volume of said α-alumina carrier is in the range of from 0.2 to 0.5 cc/g.

11. A method for the production of a silver catalyst for the production of ethylene oxide, which comprises adopting as a main raw material an alumina powder having a secondary particle diameter in the range of from 20 to 200 μm formed of primary α-alumina particles 0.11 to 10 μm in diameter and a specific surface area in the range of from 0.1 to 10 m²/g, mixing the alumina powder with alumina and silica which are in a colloidal state, molding the resultant mixture in a prescribed shape, drying the molded article and calcining it at a temperature in the range of from 1,000° to 1,600° C. thereby preparing an α-alumina carrier having the outer surface thereof and the surface of pores therein coated with an amorphous silica-alumina mixture having a total Si and Al content in the range of from $3 \times 10^{-4}$ to $2 \times 10^{-1}$ g/g of carrier and an Si/Al ratio in the amorphous mixture in said range of from 0.05 to 50.0 g/g, depositing 5 to 25% by weight based on finished catalyst of fine metallic silver particles and 0.0001 to 0.05 gram equivalent weight per kg of finished catalyst of cesium on said α-alumina carrier, activating the resultant composite, thereby effecting deposition of said silver and said cesium on the resultant porous inorganic refractory carrier, and thereafter subjecting said composite to a heat treatment in an inert gas at an elevated temperature in the range of from 400° to 950° C.

12. A method according to claim 11, wherein said carrier possesses an average equivalent diameter in the range of from 3 to 20 mm.

13. A method according to claim 11, wherein said α-alumina carrier has a porosity in the range of from 45 to 70%.

14. A method according to claim 11, wherein the cesium content is in the range of from 0.001 to 0.03 gram equivalent weight per kg of finished catalyst.

15. A method according to claim 13, wherein said α-alumina carrier possesses a specific pore volume in the range of from 0.1 to 0.8 cc/g.

16. A method according to claim 11, wherein the metallic silver content is in the range of from 5 to 20% by weight.

17. A method according to claim 11, wherein the coating of said amorphous silica-alumina mixture has a total Si and Al content in the range of from $5 \times 10^{-4}$ to $1 \times 10^{-1}$ g/g of carrier and an Si/Al ratio in the range of from 0.5 to 10.0 g/g.

18. A method according to claim 11, wherein the specific pore volume of said α-alumina carrier is in the range of from 0.2 to 0.5 cc/g.

19. A method according to claim 11, wherein said heat treatment is carried out at a temperature in the range of from 500° to 800° C.

* * * * *